(12) United States Patent
Hirai et al.

(10) Patent No.: US 8,637,238 B2
(45) Date of Patent: Jan. 28, 2014

(54) METHOD OF VERIFYING PERFORMANCE OF OPTICAL DETECTION APPARATUS AND STANDARD REAGENT USED THEREFOR

(75) Inventors: Mitsuharu Hirai, Kyoto (JP); Toshiya Hosomi, Kyoto (JP); Yuki Yoshinaga, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 663 days.

(21) Appl. No.: 12/300,510

(22) PCT Filed: Dec. 25, 2007

(86) PCT No.: PCT/JP2007/074842
§ 371 (c)(1),
(2), (4) Date: Nov. 12, 2008

(87) PCT Pub. No.: WO2008/084672
PCT Pub. Date: Jul. 17, 2008

(65) Prior Publication Data
US 2009/0113980 A1    May 7, 2009

(30) Foreign Application Priority Data

Jan. 10, 2007 (JP) ................................. 2007-002405

(51) Int. Cl.
*C12Q 1/68* (2006.01)
*C12M 1/00* (2006.01)
*C12M 1/34* (2006.01)
*C07H 21/02* (2006.01)
*C07H 21/04* (2006.01)
*G01J 1/10* (2006.01)
*G01D 18/00* (2006.01)

(52) U.S. Cl.
USPC ..... 435/6.1; 435/283.1; 435/287.2; 536/23.1; 536/24.3; 356/243.1; 73/1.01

(58) Field of Classification Search
USPC ........... 435/6.1, 283.1, 287.2; 536/23.1, 24.3; 356/243.1; 73/1.01
See application file for complete search history.

(56) References Cited

U.S. PATENT DOCUMENTS

| 6,030,115 A | 2/2000 | Ishiguro et al. | |
| 6,503,711 B1 * | 1/2003 | Krull et al. ........................ | 435/6 |
| 7,354,707 B2 | 4/2008 | Kurane et al. | |
| 2004/0081974 A1 * | 4/2004 | Gao ................... | 435/6 |

FOREIGN PATENT DOCUMENTS

| JP | 10-332701 A | 12/1998 |
| JP | 2002-119291 A | 4/2002 |
| JP | 2005-58107 A | 3/2005 |
| WO | WO2005/047468 | 5/2005 |

OTHER PUBLICATIONS

Howell et al, iFRET an improved fluorescence system for DNA melting analysis, 2002, Genome Research, 12, 1401-1407.*
Dodge et al. "A Microfluid Platform using Molecular Beacon-Based Temperature Calibration for Thermal Dehybridization of Surface-Bound DNA". *Analytical Chemistry*, vol. 76, No. 6, pp. 1778-1787 (2004).
Nellaker et al. "Molecular Beacon-Based Temperature Control and Automated Analyses for Improved Resolution of Melting Temperature Analysis Using SYBR I Green Chemistry". *Clinical Chemistry*, vol. 53, vol. 1, pp. 98-103 (2007).
Herrmann et al. "Amplicon DNA Melting Analysis for Mutation Scanning and Genotyping: Cross-Platform Comparison of Instruments and Dyes". *Clinical Chemistry*, vol. 52, vol. 3, pp. 494-503 (2006).
Li et al. "A new class of homogeneous nucleic acid probes based on specific displacement hybridization". *Nucleic Acids Research*, vol. 30, No. 2, p. e5 (2002).
International Search Report of PCT/JP2007/074842, dated Feb. 12, 2008.
Loeffler et al. "Rapid Detection of Point Mutations by Fluorescence Resonance Energy Transfer and Probe Melting Curves in *Candida* Species." Clinical Chemistry, 46:5, 2000, pp. 631-635.

(Continued)

*Primary Examiner* — Narayan Bhat
(74) *Attorney, Agent, or Firm* — Morgan, Lewis & Bockius LLP (57) ABSTRACT

A method is provided in which with respect to an optical detection apparatus including an optical detection unit and a temperature control unit, whether optical signal detection and temperature control are performed accurately, i.e. the performance thereof, can be verified simply with high reliability. With respect to an optical detection apparatus including an optical detection unit for detecting an optical signal of a sample and a temperature control unit for controlling temperature of the sample, the optical signal detection performance and temperature control performance are verified by the following method. First, a standard sample containing a nucleic acid sequence and a strand complementary thereto that have a known optical signal intensity and Tm value is provided, the temperature of the standard sample is increased or decreased with the temperature control unit, and optical signal intensity of the standard sample is measured with the detection unit. On the other hand, the melting temperature of the standard sample is determined from a change in the optical signal intensity accompanying a change in the temperature. The measured optical signal intensity and melting temperature of the standard sample are compared to the known optical signal intensity and melting temperature of the standard sample, respectively, and thereby it is verified whether the optical signal detection performance of the detection unit and the temperature control performance of the temperature control unit are accurate.

22 Claims, 1 Drawing Sheet

(56) References Cited

OTHER PUBLICATIONS

Petronis et al. "Multithermal DNA Micro-Array Chip for Rapid DNA Melting Temperature Measurement and Advanced SNP Discrimination." 18th IEEE International Conference on Micro Electro Mechanical Systems, 2005, pp. 838-841.

Office Action dated Mar. 22, 2011 for corresponding European Patent Application No. 07860071.5.

J.M. Teare et al., *Measurement of Nucleic Acid Concentrations Using the DyNA Quant™ and the GeneQuant™*, 22:6 Biotechniques 1170-74 (Jun. 1997).

Christoffer Nelløker et al., *Molecular Beacon-Based Temperature Control and Automated Analyses for Improved Resolution of Melting Temperature Analysis Using SYBR I Green Chemistry*, Clinical Chemistry 53:1, pp. 98-103 (2007).

J.M. Teare et al., *Measurement of Nucleic Acid Concentrations Using the DyNA Quant™ and the GeneQuant™*, Biotechniques, vol. 22, No. 6, pp. 1170-1174 (Jun. 1997).

Office Action issued in corresponding Chinese Patent Application No. 200780028990.8 mailed Apr. 27, 2012.

* cited by examiner

METHOD OF VERIFYING PERFORMANCE OF OPTICAL DETECTION APPARATUS AND STANDARD REAGENT USED THEREFOR

TECHNICAL FIELD

The present invention relates to a method of verifying the optical signal detection performance and the temperature control performance of an optical detection apparatus in order to verify whether detection of an optical signal of a sample and control of temperature of the sample are performed normally, and to a standard reagent used therefor.

BACKGROUND ART

Recently, a method of analyzing the melting temperature (Tm) of nucleic acid is used as a new method of detecting, for example, a polymorphism or a point mutation of a gene. Since this analysis method is performed through, for example, analysis of the melting curve of nucleic acid, it also is referred to as melting curve analysis or Tm analysis.

Generally, the Tm value is defined as follows. When a solution containing a double-stranded nucleic acid is heated, the absorbance at 260 nm increases. This is because heating releases the hydrogen bonds between both of the strands in the double-stranded nucleic acid to dissociate it into a single-stranded nucleic acid (i.e. to melt the nucleic acid). When all double-stranded nucleic acids are dissociated into single-stranded DNAs, the absorbance thereof is approximately 1.5 times that obtained at the start of heating (i.e. the absorbance of only double-stranded nucleic acids), which makes it possible to judge that melting is completed thereby. Based on this phenomenon, the melting temperature Tm (° C.) generally is defined as a temperature at which the absorbance has reached 50% of the total increase in absorbance.

The use of such properties of nucleic acid makes it possible to detect, for example, a polymorphism or a mutation at a target site as follows. That is, the following method is used. First, a mutant-type detection probe complementary to a target nucleic acid sequence containing a mutant-type target site is used to form a double-stranded nucleic acid between the aforementioned probe and a single-stranded nucleic acid to be analyzed. The double-stranded nucleic acid thus formed is then heat-treated, and signals indicating dissociation (melting) of the double-stranded nucleic acid accompanying the temperature rise are measured. Thereafter, the Tm value is determined from the behavior of the signal values thus measured, and from the Tm value thus determined, the presence or absence of a mutation at the target site is judged (see Non-patent Document 1 and Patent Document 1). The higher the homology of the double-stranded nucleic acid, the higher the Tm value, and the lower the homology, the lower the Tm value. The Tm value to serve as an assessment criterion is determined beforehand with respect to each of the double-stranded nucleic acid formed of a target nucleic acid sequence containing a mutant-type target site and a mutant-type detection probe that is 100% complementary thereto and the double-stranded nucleic acid formed of a nucleic acid sequence with a wild-type target site and the mutant-type detection probe. As described above, the higher the homology, the higher the Tm value. Accordingly, the Tm value (hereinafter also referred to as the "$Tm_m$ value") obtained in the case of the former, i.e. in the case where the target site is a mutant form, is relatively high, while the Tm value (hereinafter also referred to as the "$Tm_w$ value") obtained in the case of the latter, i.e. in the case where the target site is a wild type, is relatively low. With respect to the double-stranded nucleic acid formed of the single-stranded nucleic acid to be analyzed and the mutant-type detection probe, signals are measured as described above and, for example, a peak in signal change is detected from a prepared melting curve. When the temperature indicating this peak, i.e. the Tm value, is comparable to the $Tm_m$ value determined beforehand, the single-stranded nucleic acid and the probe are matched 100%. That is, it can be judged that in the nucleic acid to be analyzed, the polymorphism at the target site is a mutant form. On the other hand, when the Tm value indicating the peak is lower than the $Tm_m$ value determined beforehand and is comparable to the $Tm_w$ value, the single-stranded nucleic acid and the probe are mismatched by a single base. Accordingly, it can be judged that in the nucleic acid to be analyzed, the polymorphism at the target site is a wild type. Furthermore, it also can be judged whether the polymorphism is a homozygote or a heterozygote. That is, in the case of analyzing a pair of alleles, when peaks are present around both the $Tm_m$ value and the $Tm_w$ value in the melting curve, it can be judged to be a heterozygote. On the other hand, it can be judged to be a mutant-type homozygote when the peak is present only around the $Tm_m$ value, while it can be judged to be a wild-type homozygote when the peak is present only around the $Tm_w$ value.

In this analysis, a method is employed widely in which, for example, a probe labeled with a fluorescent material is used as the aforementioned probe, and the fluorescence of the fluorescent material is measured as the signal. Generally, for such a detection method that utilizes Tm analysis, an optical detection apparatus is used that includes a detection unit for detecting the optical signal of a sample and a temperature control unit for controlling the temperature of the sample, and various such products are on the market.

As described above, in the Tm analysis, since the Tm value is determined by measuring the change in optical signal accompanying a change in the temperature, two points, i.e. whether the temperature of the sample is controlled accurately inside the optical detection apparatus and whether the optical signal of the sample is detected normally, are very important. Accordingly, with respect to the optical detection apparatus, it is indispensable to verify both the optical signal detection performance and the temperature control performance in order to maintain the reliability of the analysis results. Therefore, in the case of optical signal detection, for example, a solution containing a known fluorescent material at a known concentration is provided and the signal intensity (fluorescence intensity) of the fluorescent dye in the solution then is measured under a predetermined temperature condition, and thereby it is verified whether the optical signal can be measured normally. On the other hand, with respect to the control of sample temperature, a sample is placed in a predetermined part (hereinafter, also referred to as a "sample placement part") of the optical detection apparatus and the temperature of the sample then is measured actually. Thus, it is verified whether the sample temperature is controlled accurately with the temperature control unit of the aforementioned apparatus.

However, such a conventional method requires that with respect to an optical detection apparatus, both the optical signal detection performance and the temperature control performance are verified separately, and therefore it takes time and energy. Furthermore, with respect to the optical signal detection performance, as described above, even when, for example, a highly reliable measured value that is comparable to the theoretical value was obtained by confirmatory measurement under a predetermined temperature condition, it does not serve as proof of temperature accuracy at the time of actual measurement. That is, it does not serve as proof that the sample placement part or the sample placed therein is actually at a predetermined preset temperature. Therefore, the measured value of the fluorescence intensity cannot be considered to indicate a highly reliable value at the "desired preset temperature". As a result, it is indispensable to verify the temperature control performance separately. On the other hand, the temperature of the sample placed in the optical detection apparatus is measured usually with a thermometer introduced from the outside. However, there is a possibility that the temperature may vary depending on the place where the measurement is carried out in the sample placement part. Furthermore, since the sample placement part is minute, there is a possibility that the introduction itself of the thermometer from the outside may affect the actual temperature. For such reasons, it is difficult to measure the actual temperature of a sample placed in the optical detection apparatus accurately. Consequently, it is difficult to judge whether the temperature of the sample is controlled accurately by the temperature control unit.

[Nonpatent Document 1] Clinical Chemistry 46:5 631-635 (2000)
[Patent Document 1] JP 2005-58107 A

DISCLOSURE OF INVENTION

The present invention therefore is intended to provide a method that makes it possible to verify whether optical signal detection and temperature control are performed accurately, i.e. the performances thereof, simply and with high reliability, with respect to an optical detection apparatus including an optical detection unit and a temperature control unit.

In order to achieve the aforementioned object, a method of verifying the performance of an optical detection apparatus of the present invention is a method of verifying the optical signal detection performance of a detection unit for detecting an optical signal of a sample and the temperature control performance of a temperature control unit for controlling temperature of the sample, in an optical detection apparatus equipped with the detection unit and the temperature control unit, wherein the method includes the following steps (A) to (D):

(A) providing a standard sample containing a nucleic acid sequence and a strand complementary thereto that have a known optical signal intensity and melting temperature.

(B) increasing or decreasing the temperature of the standard sample with the temperature control unit and measuring the optical signal intensity of the standard sample with the detection unit, (C) determining the melting temperature of the standard sample from a change in the optical signal intensity accompanying a change in the temperature, and (D) comparing the optical signal intensity of the standard sample measured in step (B) and the melting temperature of the standard sample determined in step (C) to the known optical signal intensity of the standard sample and the known melting temperature of the standard sample, respectively, to verify the optical signal detection performance of the detection unit and the temperature control performance of the temperature control unit.

A manufacturing method of the present invention is a method of manufacturing an optical detection apparatus equipped with a detection unit for detecting an optical signal of a sample and a temperature control unit for controlling temperature of the sample, wherein the manufacturing method includes a step of verifying the optical signal detection performance of the detection unit and the temperature control performance of the temperature control unit by a method of verifying the performance of the present invention.

A standard reagent of the present invention is used in a method of verifying the performance of an optical detection apparatus of the present invention, wherein the standard reagent contains a nucleic acid sequence and a strand complementary thereto that have a known optical signal intensity and melting temperature.

According to the method of verifying the performance of the present invention, the Tm analysis that is performed with the aforementioned standard sample is carried out using an optical detection apparatus to be evaluated and thereby both the detection unit performance and the temperature control unit performance can be verified. Specifically, the measurement results of the standard sample are compared to the known conditions (the signal intensity and Tm value) of the standard sample. For example, when they are approximately identical to each other, it can be judged that the performances of the detection unit and the temperature control unit are normal, while it can be judged that the performances are abnormal when they are different from each other. The present invention is a technique utilizing the characteristics that a double strand is formed of (hybridized from) nucleic acid and a strand complementary thereto and the double strand is dissociated (dissociated into a single-stranded nucleic acid) by a heat treatment, and they have inherent Tm values (° C.) according to the sequences thereof. The formation of a double strand, the dissociation of a double strand (dissociation into a single strand), and the reliability of Tm values are recognized well by a person skilled in the art. Therefore, it is apparent that the method of verifying the performance of an optical detection apparatus of the present invention allows the detection performance and temperature control performance of an optical detection apparatus to be evaluated with high reliability by using the Tm analysis. Although the formation of a double strand, the dissociation of a double strand, and the Tm value are known as described above, these characteristics are used merely for analyzing, for example, the sequence, mutation, or polymorphism of a target gene conventionally. The technical idea that those characteristics were used to verify the detection performance and temperature control performance of an optical detection apparatus was found by the inventors for the first time and was established by them. The method of the present invention can be carried out easily by using a standard reagent of the present invention as the standard sample. Furthermore, according to the method of verifying the performance of the present invention, it is not necessary to introduce, for example, a thermometer additionally into the inside from the outside as in the conventional case. Therefore, the problem that is caused by the introduction of a thermometer as described above does not arise. Furthermore, the method of verifying the performance of the present invention also can be used for a performance testing step in manufacturing an optical detection apparatus. As described above, the method of verifying the performance of the present invention can be considered to be a very effective technique since it allows both the optical signal detection performance and temperature control performance of an optical detection apparatus to be verified easily and simply by the same method.

BEST MODE FOR CARRYING OUT THE INVENTION

[Method of Verifying Performance]

A method of verifying the performance of an optical detection apparatus of the present invention is a method of verifying the optical signal detection performance of a detection unit for detecting an optical signal of a sample and the temperature control performance of a temperature control unit for controlling temperature of the sample, in an optical detection apparatus equipped with the detection unit and the temperature control unit, wherein the method includes the following steps (A) to (D):

(A) providing a standard sample containing a nucleic acid sequence and a strand complementary thereto that have a known optical signal intensity and melting temperature, (B) increasing or decreasing the temperature of the standard sample with the temperature control unit and measuring the optical signal intensity of the standard sample with the detection unit, (C) determining the melting temperature of the standard sample from a change in the optical signal intensity accompanying a change in the temperature, and (D) comparing the optical signal intensity of the standard sample measured in step (B) and the melting temperature of the standard sample determined in step (C) to the known optical signal intensity of the standard sample and the known melting temperature of the standard sample, respectively, to verify the optical signal detection performance of the detection unit and the temperature control performance of the temperature control unit.

The combination of a nucleic acid sequence and a strand complementary thereto contained in the standard sample is not limited, as long as it allows formation of a hybrid (formation of a double-stranded nucleic acid) and dissociation of the hybrid (dissociation into a single-stranded nucleic acid) to occur according to a change in the temperature. In the present invention, in order to judge whether the temperature is controlled accurately and further whether an optical signal is detected accurately, the Tm value of a double-stranded nucleic acid formed through hybridization of the nucleic acid sequence and the complementary strand is necessary. With respect to the Tm value, for example, a theoretical value can be calculated by a conventionally known method based on, for example, sequence information, GC content, salt concentration, etc. Examples of the known method include a nearest neighbor method and a method using the software MeltCalc (http://www.meltcalc.de/). In the present invention, the theoretical value of the Tm value can be used as, for example, a "known Tm value". Furthermore, the Tm value may be affected by, for example, not only the salt concentration in a reaction solution but also the concentrations of the nucleic acid sequence and the strand complementary thereto as well as the presence of a conjugate group (for instance, biotin or a fluorescent dye). Therefore, it is preferable that, for example, using a reaction solution containing a standard sample, a Tm value be measured beforehand with an optical detection apparatus whose detection performance and temperature control performance are normal, and it be used as the known Tm value. In addition, for example, a nucleic acid sequence and a strand complementary thereto that have an already known Tm value may be used in combination.

In the present invention, the nucleic acid sequence and the strand complementary thereto are not limited as long as they are allowed to undergo hybridization and dissociation according to a change in the temperature. Therefore, the complementary strand may be, for example, a sequence that is completely (100%) complementary to the nucleic acid sequence or a sequence that is partially different therefrom. Moreover, the complementary strand may be, for example, a strand composed only of a sequence complementary to the nucleic acid sequence, a strand including a sequence complementary to the nucleic acid sequence, or a strand composed only of a sequence complementary to a partial sequence of the nucleic acid sequence.

Examples of the nucleic acid sequence and the complementary strand include polynucleotides. Each length thereof is not particularly limited but is preferably, for example, approximately 10- to 100-mers.

At the time of use for the present invention, the nucleic acid sequence and the complementary strand that are contained in the standard sample may be in a state in which they have been hybridized (double-stranded nucleic acid) or in a state where they have been dissociated.

A preferable specific example of the combination of the nucleic acid sequence and the complementary strand is, for example, a combination of a probe labeled with a labeling substance that emits an optical signal (hereinafter also referred to as a "labeled probe") and a strand complementary thereto because it can improve the optical signal detection sensitivity. Examples of the labeled probe include a labeled probe that exhibits a signal independently and does not exhibit a signal after being hybridized and one that does not exhibit a signal independently and exhibits a signal after being hybridized. The former probe does not exhibit a signal after forming a hybrid (double strand) with a complementary strand but exhibits a signal when the hybrid is dissociated by heating and thereby the labeled probe is released. On the other hand, the latter probe exhibits a signal after forming a hybrid (double strand) with a complementary strand but the signal is reduced (quenched) when the hybrid is dissociated by heating and thereby the labeled probe is released. When using a standard sample containing such a labeled probe and a complementary strand, an optical signal may be measured in step (B), for example, under conditions determined according to the type of the labeling substance. The method of measuring an optical signal in step (B) can be determined suitably, for example, according to the type of the labeling substance and is not particularly limited. Examples thereof include absorbance (absorption intensity) measurement and fluorescence intensity measurement. The progress of melting and the Tm value can be determined by using the labeled probe and measuring a signal of the labeling substance, as in the case of the measurement of absorbance at 260 nm that indicates the melting state of the double-stranded nucleic acid (unlabeled). Since the present invention is a method of verifying the performance of an optical detection apparatus, it is particularly preferable that when the labeled probe is used, for example, the optical signal detection performance be verified using a labeling substance that is assumed to be measured with the optical detection apparatus (labeling substance to be measured).

The labeling substance is not particularly limited as described above but is preferably a fluorescent material because it is used widely. Examples thereof include a fluorescent dye (fluorophore). A specific example thereof is preferably a probe that, for example, exhibits fluorescence independently and allows fluorescence to be reduced (for example, quenched) after being hybridized. Generally, a probe that utilizes such a fluorescence quenching phenomenon is referred to as a fluorescence quenching probe. Particularly, with respect to the aforementioned labeled probe, it is preferable that the 3' end or 5' end of the probe (polynucleotide) be labeled with a fluorescent dye. Furthermore, it is preferable that the base located at the end to be labeled or a base adjacent thereto be cytosine (C). The adjacent base is preferably, for example, a base located first to third counted from the base located at the end. In this case, in the sequence of the complementary strand to which the labeled probe hybridizes, it is preferable that the base sequences of the labeled probe and complementary strand be designed so that the base to be paired with the end base C of the labeled probe or the adjacent base C be G. Generally, such a probe is referred to as a guanine quenching probe and is known as so-called QProbe (registered trademark). When such a guanine quenching probe hybridizes to a complementary strand, C located at the end of the labeled probe that has been labeled with a fluorescent dye approaches G of the complementary strand, and thereby a phenomenon occurs in which the emission of the fluorescent dye decreases (the fluorescence intensity decreases). The use of such a labeled probe makes it possible to check hybridization and dissociation easily according to a change in the signal.

The fluorescent dye is not particularly limited. Examples thereof include a fluorescein, phosphor, rhodamine, and polymethine dye derivative. Examples of commercially available fluorescent dyes include BODIPY FL (brand name, manufactured by Molecular Probe Inc.), FluorePrime (trade name, manufactured by Amersham Pharmacia), Fluoredite (trade name, manufactured by Millipore Corporation), FAM (manufactured by ABI), Cy3 and Cy5 (manufactured by Amersham Pharmacia), and TAMRA (manufactured by Molecular Probe Inc.).

Furthermore, the combination of the nucleic acid sequence and the complementary strand may be, for example, a combination of an unlabeled nucleic acid sequence and a nucleic acid sequence complementary thereto. As described above, a double-stranded nucleic acid changes in absorbance at a wavelength of 260 nm according to a change in temperature. Accordingly, when the unlabeled nucleic acid sequence and complementary strand are used as described above, it is preferable that, for example, the absorbance at 200 to 350 nm (preferably, 260 nm) be measured as the optical signal in step (B) described above. The lengths of such a nucleic acid sequence and a complementary strand also are not particularly limited and are the same as described above.

The standard sample additionally may contain, for example, an intercalator. Particularly, when a labeled probe described above is not used, it is preferable that the intercalator be contained in addition to an unlabeled nucleic acid sequence and a complementary strand. The intercalator is preferably, for example, an intercalating fluorescent material, which generally is known as a dye whose fluorescence properties change through intercalation into a double-stranded nucleic acid. Such a fluorescent dye is not particularly limited as long as the fluorescence properties thereof change through intercalation into a double-stranded nucleic acid. Particularly, a fluorescent dye whose fluorescence intensity increases through intercalation is preferable. Examples thereof include ethidium bromide, thiazole orange, oxazole yellow, and derivatives thereof. As described above, in the case of a standard sample containing the intercalator, the standard sample can be irradiated with excitation light and thereby the intensity of fluorescence generated from the intercalator may be measured in step (B) described above.

In the present invention, using, for example, two or more different standard samples, performance verification may be carried out twice or more. As described above, a hybrid formed of a nucleic acid sequence and a complementary strand has an inherent Tm value. Accordingly, when a plurality of standard samples whose Tm values are different from each other are used, it can be evaluated with respect to each of the samples whether temperature control and optical signal detection are being performed accurately. This allows the performance to be verified over more temperature ranges. Consequently, the reliability of analysis that is performed using an optical detection apparatus can be further improved.

Similarly, performance verification may be carried out using two or more standard samples that are different only in the type of the labeling substance contained in the labeled probe. For instance, when two or more fluorescent materials that are different in detection wavelength are used in actual measurement carried out using optical detection, fluorescence intensities are detected at two or more different wavelengths in one optical detection apparatus. In such a case, when the performance of a fluorescence detection apparatus is verified beforehand using two or more standard samples that are different in fluorescent material, it also is possible to perform measurement with high reliability with respect to, for example, a plurality of wavelengths. As a specific example, when the method of verifying the performance of the present invention is carried out before the analysis to be carried out at a plurality of wavelengths in, for example, an analysis method using the aforementioned Q-probe or a hybridization method, the analysis can be performed with very high reliability.

In the present invention, the type of optical signal is not particularly limited. For example, it can be fluorescence intensity or absorbance according to the presence or absence of labeling of the nucleic acid sequence or the presence or absence of intercalation.

An optical detection apparatus that can employ the method of verifying the performance of the present invention is not limited as long as it is an apparatus equipped with an optical detection unit for detecting an optical signal of a sample and a temperature control unit, and, for example, configurations, sizes, placement parts, and other constitutions of the respect units are not limited. Specifically, for example, the method of verifying the performance of the present invention is applicable to conventionally known optical detection apparatuses such as a Tm analyzer, a PCR (polymerase chain reaction) system, and a real-time PCR system.

The method of verifying the performance of the present invention is described with an example using a standard sample containing a labeled probe that has been labeled with a fluorescent dye and a strand complementary thereto. The present invention is not limited by this example.

Step (A): Provision of Standard Sample

First, a standard sample containing a labeled probe and a strand complementary thereto as described above is provided. Since a liquid sample is used generally for the Tm analysis, the standard sample is preferably a liquid containing the labeled probe and the complementary strand. The solvent for the standard sample is not limited. Examples thereof include various buffer solutions such as water, glycine, citric acid, acetic acid, phosphoric acid, and Tris, and the pH thereof is preferably in the range of, for example, 5 to 9. In addition, for example, salt, alcohol, or a surfactant may be contained.

The Tm value (known Tm value) of the hybrid between the labeled probe and the complementary strand in the standard sample can be determined beforehand by the method as described above.

The known optical signal intensity of the standard sample can be set, for example, as follows. For example, using an optical detection apparatus in which the detection performance of an optical detection unit and temperature control performance are normal, the optical signal intensity of the standard sample is measured beforehand under the same conditions as those employed for the performance verification described later. This is used as the known optical signal intensity. Specifically, when a probe labeled with a fluorescent dye is used, for example, the composition of the standard sample, the type of the fluorescent dye, the concentration of the labeled probe and complementary strand in the standard sample, the sequences of the labeled probe and complementary strand, the type of the light source for excitation light (for instance, wavelength or the amount of light), the type of detection (for instance, wavelength or detection sensitivity), and the detection temperature are specified, and fluorescent signal intensity then is measured. This measured value can be used as a known fluorescent signal intensity. Thereafter, using an identical standard sample, the fluorescent signal intensity of the standard sample is measured with an apparatus whose performance is to be verified under the same measurement conditions as those employed for determining the known fluorescent signal intensity. The detection performance can be verified by comparing this measured value to the known fluorescent signal intensity and judging whether they are comparable to each other. As described above, when verification measurement is carried out using an identical standard sample under the same conditions, it also is possible to verify the optical detection unit performance continually with high reliability in the case where, for example, the performance is verified periodically.

Step (B): Measurement of Optical Signal Intensity

Next, the standard sample thus prepared is introduced into a predetermined sample placement part (sample placement unit) of an apparatus (optical detection apparatus) whose performance is to be verified.

Subsequently, the temperature of the standard sample placed inside the apparatus is increased or decreased according to the method of operating the optical detection apparatus. The initial temperature and the final temperature are not particularly limited and can be determined according to, for example, the known Tm value of the standard sample to be employed. Generally, in the case of starting at a lower temperature than the known Tm value, the nucleic acid sequence and the complementary strand are in the form of a hybrid. Therefore, it is preferable that, for example, the temperature of the standard sample be increased to a higher temperature than the known Tm value over time to dissociate the hybrid. On the other hand, generally, in the case of starting at a higher temperature than the Tm value, the nucleic acid sequence and the complementary strand sequence are in the dissociated state. Therefore, it is preferable that, for example, the temperature of the standard sample be decreased to a lower temperature than the known Tm value over time to allow a hybrid to be formed.

In parallel with the temperature adjustment of the standard sample, the fluorescence intensity of the standard sample accompanying a change in the temperature is measured according to the method of operating the optical detection apparatus. The fluorescence intensity may be measured, for example, continuously or intermittently. However, since the present invention is intended to verify the performance, continuous measurement is preferable.

Step (C): Determination of Tm Value

The melting temperature of the standard sample is determined from the change in fluorescence intensity accompanying the change in temperature measured in step (B). Specifically, for example, from the measurement result of the change in fluorescence intensity, the Tm value ($Tm^1$) is determined based thereon.

The Tm value ($Tm^1$) can be determined from, for example, the amount of change in optical signal intensity per unit time. Specifically, for example, the amount of change in optical signal intensity per unit time at each temperature is determined first from the optical signal intensity of the standard sample measured in step (B). This amount of change can be calculated by, for example, the formula "–d amount of change in fluorescence intensity/dt" or "amount of change in fluorescence intensity/dt". The point (temperature) at which the absolute value of the amount of change in optical signal intensity is the largest value can be determined as the Tm value ($Tm^1$) of the standard sample. However, the present invention is not limited by this.

Step (D): Performance Verification

The result of Tm value thus determined and the fluorescence intensity of the standard sample thus measured are compared to the known Tm value ($Tm^0$) and the known fluorescence intensity ($F^0$) of the standard sample, respectively. Specifically, for example, from the result of the change in fluorescence intensity thus measured, as described above, the Tm value ($Tm^1$) based thereon and the fluorescence intensity ($F^1$) at the temperature ($Tm^1$) are determined and then are compared to the known values ($Tm^0$ and $F^0$). As a result, if $Tm^0 \approx Tm^1$ and $F^0 \approx F^1$, the detection performance of the optical detection unit and the temperature control performance of the temperature control unit of the optical detection apparatus can be judged to be normal. On the other hand, if $Tm \neq Tm^1$ and $F^0 \neq F^1$, the detection performance of the optical detection unit and the temperature control performance of the temperature control unit of the optical detection apparatus can be judged to be abnormal. In the present invention, the extent of approximation of the measured results $Tm^1$ and $F^1$ to the known values $Tm^0$ and $F^0$ that is judged to be normal and the extent of difference therebetween that is judged to be abnormal are not limited. The present invention is characterized in that it was found that the performance was verifiable by the Tm analysis. For example, the criterion (reference for evaluation) for determining whether the performance is normal or abnormal can be set to a desired criterion by the person who verifies the optical detection apparatus.

In the present invention, the known signal intensity of the standard sample may be, for example, the amount of change in optical signal intensity per unit time at a desired temperature. In this case, in step (D), the amount of change in optical signal intensity per unit time at a desired temperature is determined from the optical signal intensity of the standard sample measured in step (B), and then is compared to the known amount of change in optical signal intensity per unit time at the desired temperature of the standard sample. Specifically, for example, the amount of change in fluorescence intensity per unit time at the desired temperature can be determined by the formula "–d amount of change in fluorescence intensity/dt" or "amount of change in fluorescence intensity/dt" from the measured fluorescence intensity.

[Manufacturing Method]

The manufacturing method of the present invention is a method of manufacturing an optical detection apparatus equipped with a detection unit for detecting an optical signal of a sample and a temperature control unit for controlling temperature of the sample, wherein the manufacturing method includes verifying the optical signal detection performance of the detection unit and temperature control performance of the temperature control unit by a method of verifying the performance of the present invention.

The present invention is characterized by verifying the optical detection apparatus performance relating to manufacture according to the method of verifying the performance of the present invention as part of the manufacturing process, and the other configurations or conditions are not limited.

[Standard Reagent]

A standard reagent of the present invention is used for verifying the optical signal detection performance of an optical detection unit for detecting an optical signal of a sample and temperature control performance of a temperature control unit for controlling temperature of the sample in an optical detection apparatus equipped with the optical detection unit and the temperature control unit, wherein the standard reagent contains a nucleic acid sequence and a strand complementary thereto that have a known optical signal intensity and Tm value.

The standard reagent of the present invention can be used as a standard sample in the method of verifying the performance of the present invention. The above-mentioned nucleic acid sequence and the strand complementary thereto are the same as described above. For example, the composition of the standard reagent and the method of using it are the same as those employed for the standard sample.

Next, an example of the present invention is described. However, the present invention is not limited by the following example.

Example 1

First, a reaction solution having the composition described below was provided as a standard sample (standard reagent), with the reaction solution containing the labeled probe described below and a complementary strand DNA that is complementary thereto. The (BODIPY FL) located at the 5' end of the labeled probe described below is a fluorescent dye and the (P) located at the 3' end denotes phosphorylation.

TABLE 1

| <Reaction Solution> | |
| --- | --- |
| Distilled water | 19.5 |
| 10 x Gene Taq buffer * | 2.5 |
| 5 µM labeled probe | 1.0 |
| 5 µM Complementary strand DNA | 2.0 |
| Total | 25.0 µL |

* Trade name, Gene Taq Fp: manufactured by Nippon Gene Co., Ltd.

[Standard Sample]

Labeled probe
(SEQ ID NO:1)
5'-(BODIPY FL)-caccccctgaatccaggtaagg-P-3'

Complementary Strand DNA
(SEQ ID NO:2)
5'-ttggccttacctggattcaggggtgcttacaatcctgat-3'

The known Tm value and known fluorescence intensity of the reaction solution were determined beforehand as follows. An optical detection apparatus (trade name: Smart Cycler, manufactured by Cepheid) was prepared, which was of the same type as the fluorescence detection apparatus whose performance was to be evaluated, which is described later, and it was confirmed beforehand that the optical detection apparatus had a normal detection performance of the optical detection unit and a normal temperature control performance. Thereafter, using this optical detection apparatus, the fluorescence values (fluorescence intensities) in the predetermined temperature range (45~95° C.) were measured under the same conditions as those employed for performance verification described later. From the fluorescence values, the differential value "-d amount of increase in fluorescence intensity/dt" was determined that indicated the amount of change in fluorescence intensity. As a result, the Tm value of the reaction solution was 70.6° C. and the fluorescence value at 80° C. was 1072, which were used as the known Tm value and known fluorescence intensity, respectively. In the present invention, any fluorescence value obtained at any temperature can be used as the known fluorescence intensity. The fluorescence values (known fluorescence intensities) obtained at a plurality of temperatures are indicated as examples in Table 2 below.

Figure 1:
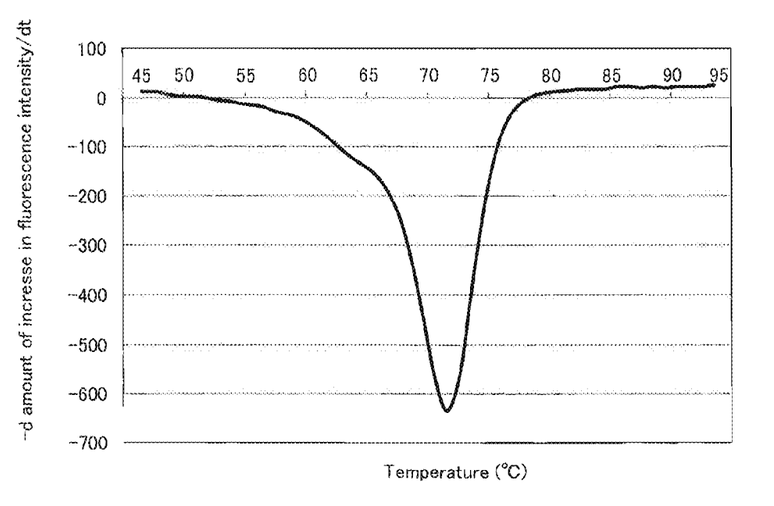
FIG. 1 shows a graph indicating the result of Tm analysis in Example 1 of the present invention.

Furthermore, a fluorescence detection apparatus whose performance is to be evaluated, i.e. a fluorescence detection apparatus (trade name: Smart Cycler, manufactured by Cepheid) whose optical signal detection performance and temperature control performance are unknown, was prepared, and Tm analysis was carried out with respect to the reaction solution. The measurement wavelengths were 450 to 495 nm (excitation) and 505 to 537 nm (emission). The results are indicated in FIG. 1. FIG. 1 is a graph of Tm analysis showing the change in fluorescence intensity accompanying the temperature rise, and the differential value indicated on the vertical axis denotes "-d amount of increase in fluorescence intensity/dt". Furthermore, fluorescence values (measured fluorescence intensities) obtained at a plurality of temperatures are indicated in Table 2 below.

TABLE 2

| Temperature (° C.) | Known fluorescence intensity | Measured fluorescence intensity |
| --- | --- | --- |
| 55 | 214 | 231 |
| 60 | 243 | 257 |
| 65 | 341 | 348 |
| 70 | 610 | 601 |
| 75 | 1054 | 976 |
| 80 | 1072 | 984 |
| 85 | 1058 | 969 |

As shown in FIG. 1, the temperature at which the peak differential value of the fluorescence intensity was obtained was 70.6° C. and was comparable to the known Tm value, 70.9° C. Furthermore, the fluorescence value at 80° C. was 984 and was almost comparable to the known fluorescence value, 1072. The above-mentioned results proved that there was no problem in either the fluorescence intensity detection performance or the temperature control performance. As described above, the method according to this example allows both the fluorescence intensity detection performance and the temperature control performance to be verified from the result of single Tm analysis.

INDUSTRIAL APPLICABILITY

As described above, the method of the present invention allows both the optical detection unit performance and the temperature control unit performance to be verified by carrying out Tm analysis with an optical detection apparatus whose performance is to be evaluated, using a standard sample. Specifically, the measurement results of a standard sample are compared to known conditions (intensity and Tm value) of the standard sample, and thereby it can be judged that, for example, the optical detection apparatus performance is accurate if they are almost comparable to each other, and the performance is inaccurate if they are different from each other. Furthermore, according to the method of the present invention, there is no need to introduce, for example, a thermometer from the outside for the temperature measurement as in the conventional case. Thus, the method of verifying the performance of the present invention allows both the optical signal detection performance and temperature control performance of an optical detection apparatus to be verified easily and simply by the same method. Thus, it is very effective technique.

[Sequence Table]
TF07043-01.5T25.txt

The invention claimed is:

1. A method of verifying the performance of an optical detection apparatus, the method comprises the following processes (A) through (H):

(A) providing an optical detection apparatus having an optical detection performance and temperature control performance that are normal;

(B) providing a standard sample containing a nucleic acid sequence;

(C) measuring a first optical signal intensity and first melting temperature of the standard sample with the optical detection apparatus having an optical detection performance and temperature control performance that are normal;

(D) providing an optical detection apparatus to be verified;

(E) measuring a second optical signal intensity of an identical standard sample with the optical detection apparatus to be verified by increasing or decreasing temperature of the identical standard sample with a temperature control unit of the optical detection apparatus to be verified;

(F) determining a second melting temperature of the identical standard sample from a change in the optical signal intensity accompanying a change in the temperature;

(G) comparing both (i) the second optical signal intensity of the identical standard sample measured in process (E) to the first optical signal intensity of the standard sample determined in process (C) and (ii) the second melting temperature of the identical standard sample determined in process (F) to the first melting temperature of the standard sample determined in process (C); and (H) determining whether the optical detection apparatus to be verified is verified or not based on the comparison in process (G).

2. The method of verifying the performance according to claim 1, wherein in process (H), the performances of the optical detection apparatus to be verified are judged to be normal when the second optical signal intensity of the identical standard sample measured in process (E) is in a predetermined range including the first optical signal intensity and the second melting temperature of the identical standard sample determined in process (F) is in a predetermined range including the first melting temperature, and the performances of the optical detection apparatus to be verified are judged to be abnormal when the second optical signal intensity of the identical standard sample measured in process (E) is outside the predetermined range including the first optical signal intensity or the second melting temperature of the identical standard sample determined in process (F) is outside the predetermined range including the first melting temperature.

3. The method of verifying the performance according to claim 1, wherein in process (G), the amount of change in optical signal intensity per unit time at a desired temperature of the identical standard sample measured in process (E) is compared to a known amount of change in optical signal intensity per unit time at the desired temperature of the identical standard sample.

4. The method of verifying the performance according to claim 1, wherein the first and second optical signal intensities are fluorescence intensities.

5. The method of verifying the performance according to claim 1, wherein in process (B), the nucleic acid sequence and a strand complementary thereto have been hybridized to form a double-stranded nucleic acid.

6. The method of verifying the performance according to claim 1, wherein the nucleic acid sequence is a labeled probe that has been labeled with a fluorescent material.

7. The method of verifying the performance according to claim 6, wherein the labeled probe is a probe that exhibits fluorescence independently and allows fluorescence to be quenched after being hybridized.

8. The method of verifying the performance according to claim 6, wherein in the nucleic acid sequence, the 3' end or the 5' end thereof has been labeled with the fluorescent material.

9. The method of verifying the performance according to claim 8, wherein in the nucleic acid sequence, a base located at the end labeled with the fluorescent material or a base adjoining the base located at the end is cytosine.

10. The method of verifying the performance according to claim 1, wherein the standard sample further comprises an intercalator.

11. A method of manufacturing an optical detection apparatus equipped with a detection unit for detecting an optical signal of a sample and a temperature control unit for controlling temperature of the sample, wherein the method comprises verifying an optical signal detection performance of the detection unit and a temperature control performance of the temperature control unit by a method of verifying the performance according to claim 1.

12. A standard reagent that is used for a method of verifying the performance of an optical detection apparatus according to claim 1, wherein the standard reagent comprises a nucleic acid sequence.

13. The standard reagent according to claim 12, wherein the nucleic acid sequence and a strand complementary thereto have been hybridized to form a double-stranded nucleic acid.

14. The standard reagent according to claim 12, wherein the nucleic acid sequence is a labeled probe that has been labeled with a fluorescent material.

15. The standard reagent according to claim 12, further comprising an intercalator.

16. The standard reagent according to claim 14, wherein the labeled probe is a probe that exhibits fluorescence independently and allows fluorescence to be quenched after being hybridized.

17. The standard reagent according to claim 14, wherein in the nucleic acid sequence, the 3' end or the 5' end thereof has been labeled with the fluorescent material.

18. The standard reagent according to claim 17, wherein, in the nucleic acid sequence, a base located at the end labeled with the fluorescent material or a base adjoining the base located at the end is cytosine.

19. The method of verifying the performance according to claim 1, wherein the nucleic acid sequence is SEQ ID NO:1 and a strand complementary thereto is SEQ ID NO: 2.

20. The method of verifying the performance according to claim 1, wherein the standard sample is used as the identical standard sample.

21. A method of verifying the performance of an optical detection apparatus, the method comprises the following processes (D) through (H):

(D) providing an optical detection apparatus to be verified, different from an optical detection apparatus having an optical detection performance and temperature control performance that are normal;

(E) measuring a second optical signal intensity of an identical standard sample with the optical detection apparatus to be verified by increasing or decreasing temperature of the identical standard sample with a temperature control unit of the optical detection apparatus to be verified, the identical standard sample containing a nucleic acid sequence and having the same optical signal intensity and melting temperature as a first optical signal intensity and first melting temperature of a standard sample measured with the optical detection apparatus having an optical detection performance and temperature control performance that are normal;

(F) determining a second melting temperature of the identical standard sample from a change in the optical signal intensity accompanying a change in the temperature;

(G) comparing both (i) the second optical signal intensity of the identical standard sample measured in process (E) to the first optical signal intensity of the standard sample determined in the optical detection apparatus having an optical detection performance and temperature control performance that are normal and (ii) the second melting temperature of the identical standard sample determined in process (F) to the first melting temperature of the standard sample determined in the optical detection apparatus having an optical detection performance and temperature control performance that are normal; and (H) determining whether the optical detection apparatus to be verified is verified or not based on the comparison in process (G).

22. The method of verifying the performance according to claim 21, wherein the standard sample is used as the identical standard sample.

* * * * *

```
                         SEQUENCE LISTING

<160> NUMBER OF SEQ ID NOS: 2

<210> SEQ ID NO 1
<211> LENGTH: 22
<212> TYPE: DNA
<213> ORGANISM: Artificial
<220> FEATURE:
<223> OTHER INFORMATION: probe

<400> SEQUENCE: 1 cacccccctga atccaggtaa gg                                          22

<210> SEQ ID NO 2
<211> LENGTH: 40
<212> TYPE: DNA
<213> ORGANISM: Artificial
<220> FEATURE:
<223> OTHER INFORMATION: complementary oligonucleotide

<400> SEQUENCE: 2
ttggccttac ctggattcag ggggtgctta caatcctgat                        40
```